(12) United States Patent
Loomis et al.

(10) Patent No.: US 7,514,039 B2
(45) Date of Patent: Apr. 7, 2009

(54) SYSTEM AND METHOD FOR DETECTION OF A TARGET SUBSTANCE

(76) Inventors: Charles E. Loomis, 8406 Benjamin Dr., Suite J, Tampa, FL (US) 33634; Bryan Truex, 521 Belle Isle Ave., Belleair Beach, FL (US) 33786

( * ) Notice: Subject to any disclaimer, the term of this patent is extended or adjusted under 35 U.S.C. 154(b) by 939 days.

(21) Appl. No.: 10/475,157

(22) PCT Filed: Jul. 18, 2002

(86) PCT No.: PCT/US02/23309

§ 371 (c)(1),
(2), (4) Date: Mar. 16, 2004

(87) PCT Pub. No.: WO03/008942

PCT Pub. Date: Jan. 30, 2003

(65) Prior Publication Data

US 2004/0141879 A1    Jul. 22, 2004

Related U.S. Application Data

(60) Provisional application No. 60/306,469, filed on Jul. 18, 2001.

(51) Int. Cl.
*G01L 21/00* (2006.01)
(52) U.S. Cl. ..................... 422/62
(58) Field of Classification Search .......... 422/62
See application file for complete search history.

(56) References Cited

U.S. PATENT DOCUMENTS

| | | | |
|---|---|---|---|
| 3,772,518 A | 11/1973 | Murayama et al. | |
| 3,861,879 A | 1/1975 | Taylor | |
| 3,923,462 A * | 12/1975 | Cavanagh | 436/172 |
| 4,235,097 A | 11/1980 | Kring et al. | |
| 4,551,425 A | 11/1985 | Zemel | |
| 4,557,603 A | 12/1985 | Oehler et al. | |
| 4,593,197 A | 6/1986 | Miyatake et al. | |
| 4,654,127 A | 3/1987 | Baker et al. | |
| 4,913,881 A | 4/1990 | Evers | |

(Continued)

FOREIGN PATENT DOCUMENTS

EP    0142481 A2 * 11/1984

(Continued)

*Primary Examiner*—Walter D Griffin
*Assistant Examiner*—Bobby Ramdhanie
(74) *Attorney, Agent, or Firm*—Goldizen & Associates; Bradley D. Goldizen (57) ABSTRACT

A system for the measurement of a target substance is provided including a detection apparatus and a reading apparatus. The detection apparatus, or "carrier", includes a pyroelectric film transducer ("pyroelectric film") and one or more reagent concentrations ("reagent deposits") deposited on the film. The reagent deposits are adapted to react with, and thus, detect the presence of a target substance present in the local environment. Upon detection of the target substance by the reagent deposit, the reading apparatus and the pyroelectric film may be used to detect the amount of heat that can be absorbed by the reagent in response to illumination. The pyroelectric film then delivers to the reader a signal corresponding to the heat detected and the reader provides a corresponding indication of the concentration of the target substance detected.

50 Claims, 4 Drawing Sheets

U.S. PATENT DOCUMENTS

| | | |
|---|---|---|
| 4,933,144 A | 6/1990 | May |
| 4,938,593 A | 7/1990 | Morris et al. |
| 4,941,742 A | 7/1990 | Schrader et al. |
| 5,069,879 A | 12/1991 | Leichnitz et al. |
| 5,089,232 A | 2/1992 | May |
| 5,108,576 A | 4/1992 | Malmros et al. |
| 5,397,538 A | 3/1995 | Stark et al. |
| 5,464,588 A | 11/1995 | Bather et al. |
| 5,622,868 A | 4/1997 | Clarke et al. |
| 5,923,421 A | 7/1999 | Rajic et al. |

FOREIGN PATENT DOCUMENTS

| | | |
|---|---|---|
| WO | WO 9013017 A1 * | 11/1990 |

* cited by examiner

SYSTEM AND METHOD FOR DETECTION OF A TARGET SUBSTANCE

BACKGROUND OF THE INVENTION

This application claims the benefit of U.S. Provisional Application No. 60/306,469, filed Jul. 18, 2001 (hereby incorporated by reference for all purposes).

The present invention relates generally to an apparatus, system, and method of detecting a target substance, such as a gas, in a local environment. More particularly, the invention is such a system, apparatus, and method which employs or incorporates pyroelectric film technology.

It is often desirable, advantageous, or simply necessary to monitor the environment around a work place, home, or other sites. For example, in many industrial environments, hazards may exist in the form of toxic chemicals. This is especially a concern when the harmful chemicals or substances are not readily detectable, e.g., odorless or invisible. Thus, in these environments, the air surrounding a work place may be constantly monitored by safety personnel equipped with portable testing equipment, including gas detectors. Alternatively, personnel may be required to wear or carry gas detectors, such as badges which typically provide a visual alarm when certain levels of the harmful chemicals are detected. In addition, monitoring equipment may be permanently placed at strategic locations.

The above-described applications are just some of the applications suitable for the present invention.

SUMMARY OF THE INVENTION

In one aspect of the present invention, a system for the measurement of a target substance is provided. The system includes a detection apparatus and a reading apparatus. The detection apparatus, or "carrier", includes a pyroelectric film transducer ("pyroelectric film") and one or more reagent concentrations ("reagent deposits") deposited on the film and adapted to react with, and thus, detect the presence of a target substance present in the local environment. Upon detection of the target substance, the reagent deposit is adapted for exposure to a light emitting source. The pyroelectric film detects the light absorption of the reagent deposit as microscopic heating. This microscopic heating produces an output that is processed to derive the measurement of the target substance. In this manner, the pyroelectric film is used to indicate the amount of or concentration of the target substance in the environment. This technology is described in U.S. Pat. No. 5,622,868, which is hereby incorporated by reference for all purposes and made part of the present disclosure.

A reading apparatus is provided that is operable with a detection apparatus described above. Such a reading apparatus includes a an optical device on light emitting source that is operable with the pyroelectric film and reagent deposit to indicate the amount or concentration of the target substance. The reading apparatus and the detection apparatus may be two distinct devices or may be incorporated into a single device.

As used herein, the term "indication" or "indicating" shall mean measuring, monitoring, or otherwise visually or audibly communicating the detection of the target substance to the user, including the measurement and display of the amount or concentration of the target substance in the local environment or the detection of a specified amount or concentration of the target substance. Also, as used herein, a "reagent deposit" shall mean a concentration of reagent applied to a surface and shall not be limited to any specific shape, form, or quantity.

A system according to the invention will include a carrier having one or more reagent deposits deposited thereon. In one embodiment, the reagent deposits are arranged in predetermined sets, with the sets provided in containers. The system further includes pyroelectric film positioned adjacent the reagent deposits, and a reader operatively associated with the pyroelectric film (e.g., including a light emitting source for illuminating the reagent deposit). Note that a set of reagent deposits may consist of one reagent deposit. The system may also include a pump (or some other means of moving air, such as a fan) for moving a sample of the local environment past or in the vicinity of the container containing the set, so as to initiate a reaction and detection of the target substance. Among other elements, the preferred system may also include a filter operable with the pump and/or one or more alarms for indicating the presence of a predetermined amount or concentration of the target substance.

In yet another aspect of the invention, a carrier of the pyroelectric film (e.g., a cartridge) is provided that is receivable or mateable with a reading device (including a light emitting source). The carrier or cartridge includes one or more non-exposed reagent concentrations that are exposed upon receipt or mating of the cartridge with the reading device such that detection of (and/or measurement of) the target substance can occur. In various embodiments of the invention, reagent deposits may be positioned in predetermined sets. A set may consist of a plurality of reagent deposits arranged in a row, or other pattern. In one specific embodiment, one or more reagent deposits are encased in protective coating or casing that is pierced, or otherwise compromised, upon receipt or mating of the carrier supporting the reagent concentrations with a reading apparatus. In this way, one or more reagent deposits may be exposed to the environment containing the target substance. To facilitate the use of the carrier and the reading device, the reading device may be equipped with a means for piercing the encasing upon proper receipt or mating of the carrier with the reading device.

In a further embodiment, the reading device includes a pump and air channel or conduit. Again, upon receipt or mating of the carrier with the reading device, a pump (or other means of moving air past the reagent concentrations) is operable to fluidly communicate with the container containing the sets of reagent deposits and allow for the moving of air or sample of the local environment to the vicinity of the reagent deposits. In this regard, the carrier may be keyed with the reading device so as to position the encasing in correspondence with the air channel and pump.

The present invention is further directed to a method of employing the system and/or the system described. Such an inventive method allows for the detection and indication of one or more target substances (e.g., target gas). In another embodiment, the method allows for the indication of the amount or concentration of the target substance in real-time. Thus, in one aspect of the invention, the method provides for the substantially simultaneous detection and indication of the target substance in the local environment.

DETAILED DESCRIPTION OF THE INVENTION

Figure 1:
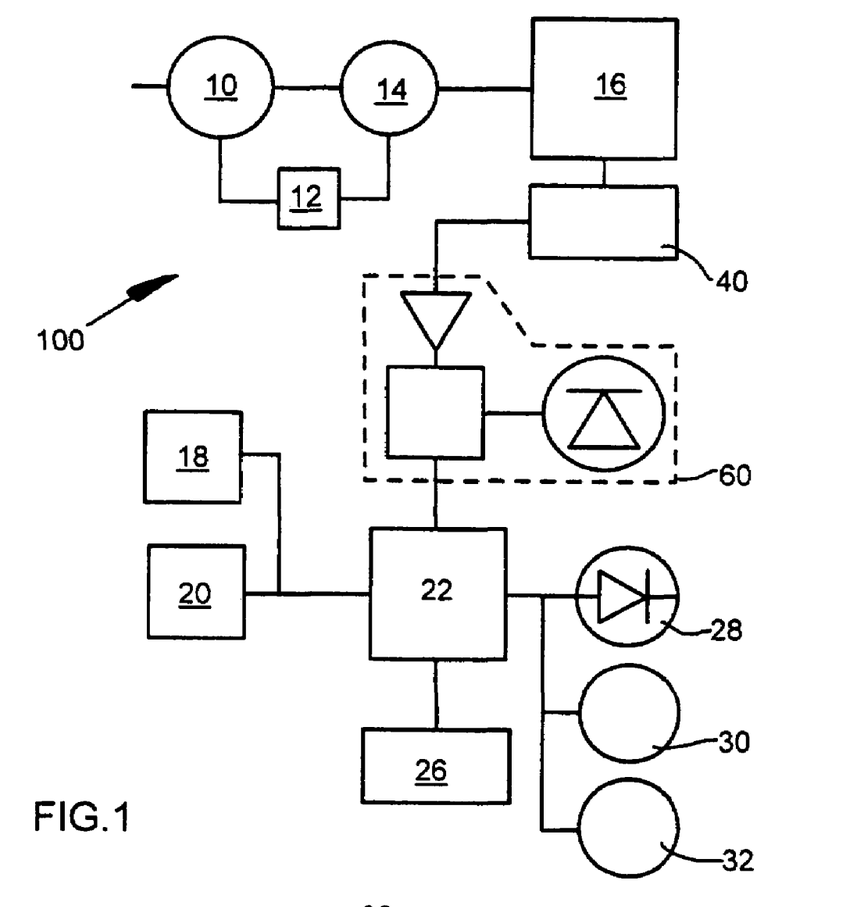
FIG. 1 is a simplified schematic representation of a gas detection system and apparatus according to the invention.

FIG. 1 is a schematic representation of a system 100 for detecting a target substance in a local gaseous or liquid environment embodying various aspects of the present invention. In a preferred embodiment, the system 100 is operable to indicate the amount or concentration of the target substance that is detected. The invention is also directed to a method of detecting such a target substance employing a combination of technologies and/or functions, most of which are provided by the system 100 represented by FIG. 1.

As will become apparent, the present invention is adapted for various applications. For example, the detection system 100 has applications in the general chemical detection market, particularly in the gas detection market, as a portable or field carryable gas detector. In this market, one of the more frequently used portable gas detectors comes in the form of badges covered with reagents that react colorimetrically with gases in the local environment. The badges are worn by the user and can provide a visual signal, in the form of a color change, when the reagent is exposed to the target gas. At most, these badges provide only an approximate measurement of the amount of gas in the local environment, relying on the user to compare or evaluate the degree of color change. The system (s) 100 depicted in the Figures provide a preferable replacement for these badges.

Figure 2:
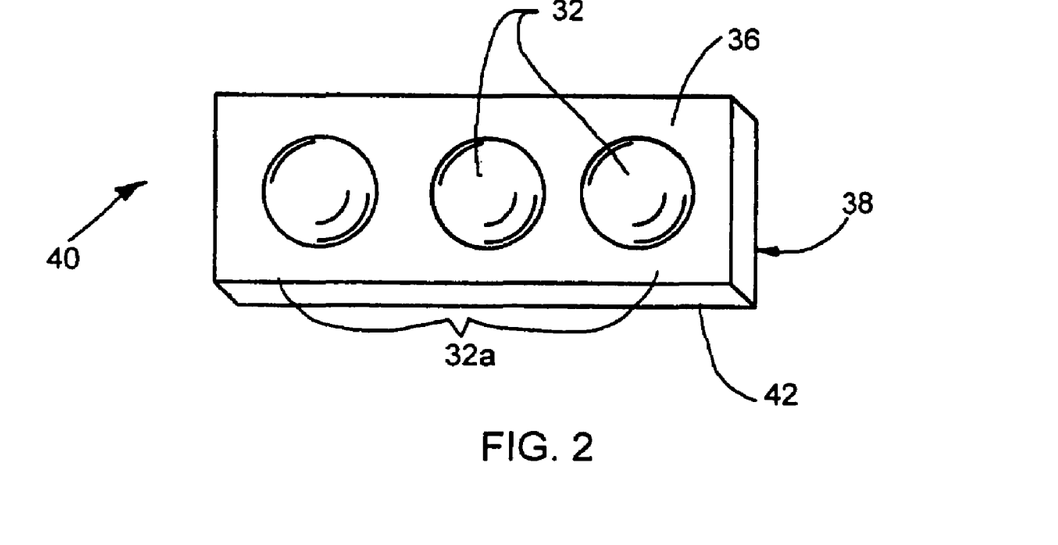
FIG. 2 is a simplified perspective view of a carrier suitable for use with the system in FIG. 1.
Figure 3A:
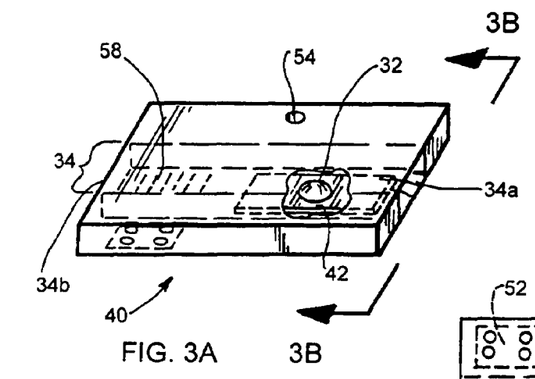
FIG. 3A is a simplified perspective view of a second carrier suitable for use with the system in FIG. 1.
Figure 3B:
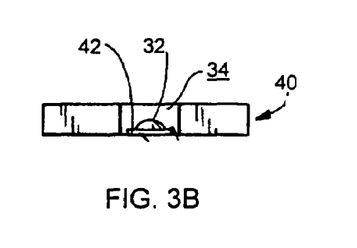
FIG. 3B is an end view of the carrier at line 3B-3B in FIG. 3A.
Figure 3C:
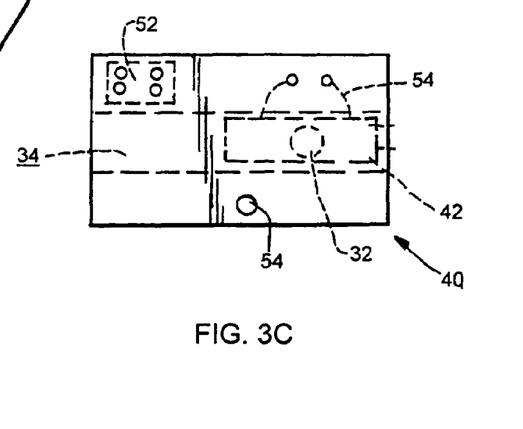
FIG. 3C is a bottom view of the carrier in FIG. 3A.

In one aspect of the invention, the inventive detection system 100 employs or incorporates a core detection component provided by: an optically detectable or calorimetric detection element, a pyroelectric or other thermoelectric transducer element operatively associated with the colorimeteric detection element, and one or more carriers or substrates 40 supporting or containing these two elements (see FIG. 1). Pyroelectric film (also called polyvinylidine fluoride (PVDF) or piezo film) suitable for use with the present invention is described generally in U.S. Pat. No. 5,622,868 (hereby incorporated by reference). One type of carrier 40 that is suitable for use with the inventive system is a cartridge-type carrier 40 as shown in FIGS. 2 and 3. Other types of carriers 40 also suitable for use with various embodiments of the invention are shown throughout in FIGS. 4-8. These other types and the corresponding Figures are described separately below.

Returning now to the schematic representation of FIG. 1, the detection system 100 includes a mechanism configured to receive an output from the transducer element 40 and to convert the output into a readable indication of the amount or concentration of the target substance detected. FIG. 1 illustrates one type of mechanism—a piezofilm reader 60—that is suitable for use with the carrier 40 of the inventive detection system 100.

The reader 60 includes an LED light source to illuminate the reagent 32. The light is pulsed with a specific frequency—approximately 50 hertz. The electrical signal produced by the heat absorbed by the colorimetric area of the pyroelectric film, is interpreted by an analog to digital converter which is then processed by a microprocessor and then displayed as a reading. This microprocessor may have additional duties relating to pump control, temperature and humidity compensation of the PVDF reading, reading and writing the memory chip stored in the PVDF film cartridge (as outlined in this patent), control of alarm indicators such as visual, audible and vibration devices, and reading optional bar code on sensor and/or filter module. In any case, a reader suitable for use with the present invention is one that incorporates many of the basic mechanisms as described in U.S. Pat. No. 5,622,868.

FIG. 1 further illustrates the use of a pump 10 in conjunction with a flow sensor 14 and flow regulator 12 for drawing and then controlling a flow of the local gaseous environment into or across the carrier 40. A flow filter 16 may be recommended as well in certain demanding environments. As further explained below, the use of a pump 10 in the detection system 100 allows for measurements which are exceedingly more accurate and consistent than currently provided by the above-mentioned badges and other known detection systems.

Depending on the requirements of a particular application, the detection system 100 may include a number of sensors, alarms and other instrumentation, each of which is operable with or linked to a control mechanism 22, as shown in FIG. 1. For example, the detection system may include a digital display 26 for visually indicating the concentration of the target substance, and one or more visual alarms 28 (e.g., flashing red LED), audible alarms 30, and vibration alarm 32. The alarms may be configured to activate when certain levels of the target substance are detected. The detection system 100 may also include a temperature sensor 18 and a humidity sensor 20.

Figure 4:
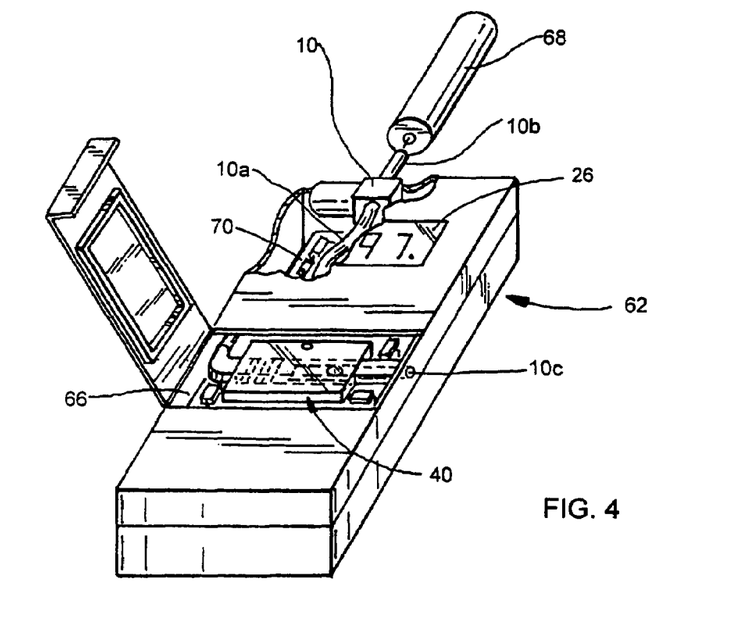
FIG. 4 is a perspective view of a receiver and carrier according to the invention.

In several embodiments, including the embodiment depicted in FIG. 4, a portable, self-contained housing 62 is provided to house or frame the piezofilm reader 60 and the various sensors, alarms, pump-related components, and other accessories. This housing 62 also includes a microprocessor or equivalent means for performing or controlling various functions, including conversion of pyroelectric film output to a readable digital indication. This self-contained housing 62 may be referred as to as the carrier receiving device or simply, the reader 62. In several embodiments, engagement between the carrier 40 and the reader 62 also initiates sampling of the local environment and testing for the target substance in that sample. Also, in several embodiments, the reader 62 is adapted to be a field-carryable, portable testing equipment.

Figures 5, 9:
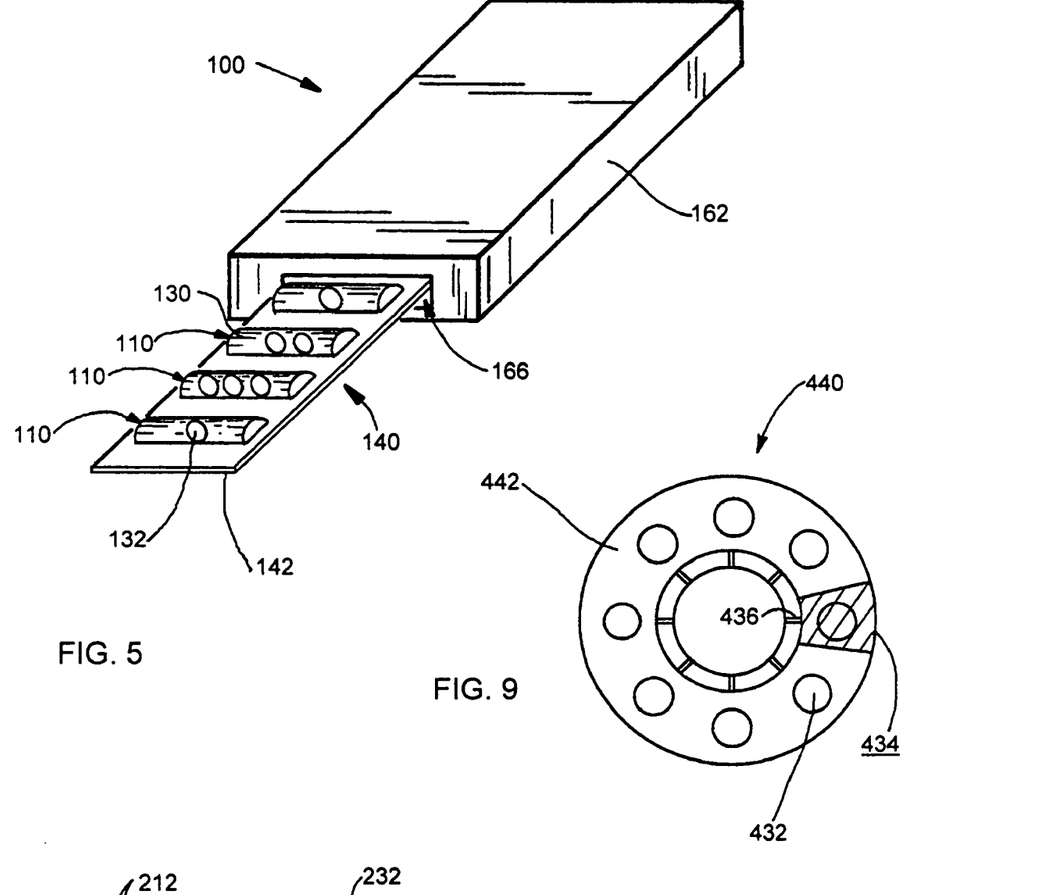
FIG. 5 is a perspective view of a second combination of a receiver and a carrier according to the invention.
FIG. 9 is a simplified diagram of a fourth carrier suitable for use with the system.

Referring now to FIGS. 2-5, the cartridge-type carriers 40 depicted therein are separate from the reader 62 but is engageable therewith during a testing operation (and detacheable therefrom for another testing operation). FIG. 4 depicts the carrier 40 in engagement with a flip-top type reader 62. FIG. 5 depicts another cartridge-type carrier being disengaged from a second type of reader 62.

The carrier 40 preferably employs a colorimetric detectable element in the form of reagents 32 that selectively react with chemicals, or target substances, in the gaseous environment. The reagents are also characterized by the amount of light it can absorb, which translates to microscopic heating generated within the reagent. Thus, the reagent may be illuminated with an LED to cause heat to be generated within the reagent. In turn, a pyroelectric film transducer is employed to measure the voltage change across the reagent which directly corresponds to the heat generated. Upon exposure to the target substance, the reagent deposit undergoes a color change, and as a result of the color change, the reagent deposit's capacity to absorb light also changes. Thus, the reagent deposit may be illuminated before and after a testing operation and the corresponding calorimetric change and the difference in the heat generated in the reagent calculated. The calculated voltage change is then translated into a corresponding concentration of the measured gas ("target gas") by the reader 62.

In one aspect of the invention, the system 100 provides for the pyroelectric film transducer/reagent to be re-set or baselined. This means that, after a detection of the target substance and corresponding color change in the reagent, the reader stores voltage measured after the reagent is illuminated by a given LED. In this way, if a subsequent LED illumination does not result in a larger amount of heat being detected (i.e., because of no further colorimetric change in the reagent), the output signal may be recognized as the same as that received in the previous illumination, and thus the reader will not indicate erroneously that the target substance has again been detected. On the other hand, if additional exposure caused the reagent to further react colorimetrically, then the voltage measured would be different and the difference in voltage can be used to indicate the concentration detected.

The above-described resetting or baseline method is just one example of a suitable method that allows the reagent to be repeatedly illuminated and exposed a plurality of times. In each case, the system 100 effectively stores in memory the amount of heat (or corresponding voltage) that a reagent absorbs in response to an LED illumination. This allows the reagent to be reused, and be used longer in the field. This also allows the system to discriminate between different degrees of exposures. It is important to note, however, that the resetting or baselining described above requires the reagent to be non-reversible (does not revert back to its original color).

In yet another aspect of the inventive testing method, a non-reversible reagent/pyrolectric film is used in combination with a continuously running pump. The pump is operated to continuously sample the local gaseous environment while the LED of the piezoptic reader is activated to illuminate intermittently. Whenever a target substance is detected, causing a colorimetric reaction and subsequent reading of the concentration detected, the reagent/pyrolectric film is reset or baselined. In this manner, the system 100 may be used for continuous monitoring in the field and for multiple exposures.

FIG. 2 provides the basic structure of a carrier 40 for use with the system 100 according to the invention. The carrier 40 of FIG. 2 includes a plurality of colorimetrically-reactive reagent deposits 32 deposited thereon. Different types of reagent deposits 32 may be selected such that one testing operation can detect a corresponding plurality of target substances. The reagent deposits 32 are preferably arranged in predetermined sets 32a. In one preferred embodiment, the system 100 includes a series of distinct reagent deposits 32 provided in the same set 32a, such that several target substances may be tested at the same time. Alternatively, a predetermined set 32a may consist of one reagent deposit (see e.g., FIG. 3a).

The carrier 40 further includes a pyroelectric film transducer 42 on which the reagent deposits 32 are deposited. The reagent deposits 32 may be deposited directly on the pyroelectric film transducer 42 using an ink jet printer or a screen print system. The pyroelectric film transducer 42 has a top surface 36 and a bottom surface 38. In embodiment of FIG. 2, the top and bottom surfaces 36, 38 provide the electrodes by which an electrical signal may be outputted from the carrier 40.

FIGS. 3a-3c depict a variation of a carrier 40 according to the invention. To facilitate description, the cartridge 40 of FIG. 3 is shown with only one reagent deposit 32. The reagent deposit 32 is contained or housed within an initially sealed tunnel 34, as best shown in end view of FIG. 3c. The tunnel 34 is essentially an elongated conduit extending the length of the cartridge 40 providing for fluid communication between the pump 10 and the local gaseous environment. Preferably, the tunnel 34 also contains a filter 58. The tunnel 34 further includes an inlet end 34a and an outlet end 34b, which provides a conduit for passage of the sampled gaseous environment. The inlet and outlet ends may be sealed by a plastic film or the like. As further described below, upon engagement of the cartridge 40 with the reader 62, the sealed inlet end 34a and outlet ends 34b are simultaneously punctured, thereby creating the fluid conduit and allowing for exposure of the reagent 32.

Referring to the end view of FIG. 3b, the pyroelectric film transducer 42 is provided as a mat situated along the bottom portion of the tunnel 34, thereby providing a bed or support for the reagent 32. In one variation of the cartridge 40, the cartridge 40 is made of glass such that the bottom surface on top surface of the tunnel is sealed by a glass surface. In further embodiments, the top end may be sealed by a plastic film.

Now referring to the bottom view of FIG. 3c as well, the carrier or cartridge 40 also includes an embedded memory chip 52 with leads or pins mateable with the reader 62. The memory chip 62 may be used to communicate the characteristics of the reagent 32 dot as well as the testing protocol or procedure for the target substance. The bottom view of FIG. 3c also shows lead lines 54 and connectors extending from the pyroelectric film. The connectors are situated so as to be mateable with corresponding connections on the piezoreader 60. Further, the cartridge 40 is also provided with a key/alignment hole or pin 56 for aligning the cartridge 40 with a corresponding hole or pin of the reader 60.

FIG. 4 shows the cartridge of FIG. 3 engaged within a receiving compartment or bay 66 of the fliptop reading device 60. When properly situated in the compartment, as provided by aligning the key alignment hole with the corresponding key alignment pin of the reader, the connectors 54 for the pyroelectric film 42 and those for the memory chip 52 align with and connect with corresponding connections on the piezoreader 60. Moreover, the inlet and outlet ends of the tunnel 34 of the cartridge 40 align with corresponding conduits integrated with the reader 62. Moreover, a tab device provided on the compartment may be positioned so as to puncture the inlet and outlet ends 34a, 34b. In this way, operation of the pump 10 draws a sampling of the local gaseous environment through the tunnel 34, thereby exposing the reagent 32 and initiating a colorimetric change therein. FIG. 4 also illustrates the use of a pump 10 having a pumping conduit 10a connecting the cartridge with the pump 10, and also with the sampling inlet 10b and outlet 10c.

The display 26, shown in FIG. 4 is a standard LCD display, and may be alphanumeric or graphical depending on what information is necessary to display. The display 26 provides the user with a numeric indication of the measurement of the concentration of the target substance (either direct immediate exposure or long term dosimeter readings). The display 26 may also display text and graphics of alarms, menus for device settings including alarm points, time, date, data-logging, gas name, sensor name, and filter name.

The pump 10 may be a fan, air pump, or other device that is capable of moving air. The pump may be located on either the intake air path before the reagent or located in the exiting air path. The pump 10 may be operated continuously or intermittently, or may be turned on for a specific amount of time for purposes of obtaining a reading or to minimize power consumption. Alternatively, the pump may be known to operate at a specific flowrate.

In the preferred embodiment of the invention, the pump 10 is used with the flow regulator 12. If the invention did not employ a flow regulator 12, the pump would be used as an uncontrolled air source that would indicate the presence of a gas, but the measurement of the amount of the target gas would not be as accurate as a measurement taken with a flow regulator 12. The flow regulator 12 can either use feedback from the motor or from the flow sensor 14. A preferred method is to control electrical power to the pump device with a feedback from the flow sensor. Such regulation may consist of controlling the pump speed and/or the on and off time of the pump in either a pulsed fashion or on for a specific time period. The flow regulator consists of an electric circuit that interfaces with the flow sensor 14 (or motor feedback) and provides power to the motor directly.

The inventors have discovered that the use of a pump 10 in combination with colorimetric and pyroelectric technology provides certain benefits. For example, the use of a pump speeds up the reaction time of the reagent and allows for a virtually instantaneous measurement of the level of the target substance in the local environment.

Furthermore, precise control of the pump, as in the present invention, provides measurements exceedingly more accurate than is achievable with prior art systems and methods. This achievement by the inventors stems from the understanding that the discoloration or stain produced by the calorimetric reaction in the reagent is proportionally relevant to the amount of air or gas that is contacted with the reagent surface. With prior art colorimetric reactions, the air or gas is contacted with the reagent through simple diffusion—which has to be timed in order to provide an acceptable, accurate measurement. In the present inventive system and method, the flow rate of the pump can be measured and/or controlled, as well as the pumping duration, and thus, the amount of air or gas contact with the reagent can also be measured and/or controlled. As a result, a high level of accuracy in measurements can be achieved and repeated. Moreover, use of the pump to initiate or encourage contact provides higher precision than the use of simple diffusion because the diffusion rate is typically affected and varied by external conditions, including wind.

In certain embodiments, a measurement device may be used to measure the amount of local environment delivered by the pump. If the pump 10 operates at a known flowrate, the measurement device could consist of a timer to time the length of operation of the pump and a converter to convert the flowrate and the pump operation time to a volume of local environment delivered. The flow sensor 14 may be provided as the optional measuring device to provide feedback to the flow regulator 12. The preferred method of flow sensing employs a differential pressure sensor. A wide range of sensors, including electromechanical sensors, hot wire sensors, and many others can be used.

Further, the reader 62 preferably includes a circuit board or other support 70, which includes the piezoptic reader 60, as well as the control mechanism 22. When the cartridge 40 is received in the bay 66, it is situated over the board 70, and such that LED's provided on the board advantageously align with the reagents 32. In further embodiments, multiple LED of various colors may be employed in combination with a light pipe for selectively illuminating the reagent with a variety of light sources. The board 70 also includes contacts for the memory chip 52 such that reagent information and testing requirements may be communicated to the reader 62.

FIG. 5 depicts yet another reader 162 and carrier 140 combination, according to the invention. The carrier 140 is shown being disengaged or detached from the receiving bay 166 of the reader 162. The carrier 140 includes one or more containers 110, each containing a set of reagent deposits 132. Preferably, the container 110 is a channel that is particularly adapted to fluidly communicating the local environment with the selected set of reagent deposits 132.

In one embodiment, the carrier 140 may be fed into the reader 162 by an electric motor. In another embodiment, the carrier 140 may be fed through operation of some type of ratchet or manually fed by hand. The carrier 140 may be made of a firm, durable plastic and may contain a barcode, magnetic stripe or embedded memory chip to identify the specific carrier 40 and the target substances and ranges it is capable of detecting.

The system further includes a means for selecting or designating a predetermined set of reagent deposits 132 for exposure to the local environment containing the target substance. In this manner, the user determines what target substance(s) to test for. Upon engagement of the carrier 140 with the reader 162, the selecting means penetrates the container 110 containing one set of reagent deposits, thereby exposing the selected reagent deposits to the local environment as further discussed below.

The system 100 embodies a reagent deposit 132 which due to its limited quantity is easily and quickly reacted upon exposure to air and humidity, causing a short "shelf life." In another embodiment, each container 110 containing a set of reagent deposits 132 is covered by a shield 130, shown in FIG. 5 as a tunnel, to shield the reagent deposits 132 from the local environment until the carrier 140 is engaged with the reader 162. Upon engagement of the carrier 40 with the reader 60, the shield of the selected set of reagent deposits 132 is penetrated or compromised, allowing exposure of the selected set of reagent deposits 132 to the local environment containing the target substance. The tunnel is preferably made of glass, but could also be made of another rigid material such as mylar or polyvinylchloride. The ends of the tunnel are preferably covered with film that may be compromised or punctured to expose the container 110. Alternatively, the shield 130 could consist of a film covering each container 110. In one aspect of the invention, the shields (either in the form of a film covering or a tunnel) allow for multiple testing procedures using the same carrier 140. During a testing operation only the selected set of reagent deposits 132 are exposed, leaving the remaining sets of reagent deposits unexposed underneath the shield. The shield-compromiser preferably consists of a sharp implement to puncture the film-covered ends of the tunnel or the film.

In another embodiment of the invention, a filter is used to filter out interferences from the local environment containing the target substance before the local environment comes in contact with the selected set of reagent deposits. Filters generally improve the specificity and accuracy of the colorimetric and target gas interaction. The filter may be a variety of materials and coatings to specifically filter interferences (through membranes that restrict particle size, chemicals that react with, remove, or change a chemical compound into another chemical that will not interfere with the target gases) from the selected set of reagent deposits. Specific filters could include a hydrophobic filter to remove humidity, a filter to screen out toluene and xylene from benzene and air, a filter to remove chlorine gas from a mixture of chlorine dioxide and air, and many others.

These filters may be used individually or in combination as needed to filter interferences from the selected set of reagent deposits 23. Further uses of such filters will be apparent to one skilled in the art upon review of the present disclosure.

One kind of filter that may be used is a column or a long glass tube is coated with a substance that temporarily bonds with specific target substances. The temporary bonds are subsequently released when heat is applied to the column. Because of the temporary nature of chromatographic columns, this type of filter is preferably used in the portable embodiment of the system, but not the fixed embodiment. This type of filter has the advantage of temporarily holding back the interfering substance during the measurement of the primary target chemical, but then allowing the measurement of the interfering substance when it is released from the column when heat is applied.

In yet another aspect of the invention a specific type of filter is designed to change the target compound into a gas that will have a calorimetric reaction. This is accomplished by a providing a chemical layer that reacts with the target substance and changes, through a chemical reaction, the target substance into a gas that then reacts colorimetrically with the reagent deposits on the pyroelectric film sensor strip. This can be accomplished with many target compounds, including methyl bromide, which is broken into bromine through reaction with sulfuric acid. The bromine then reacts colorimetrically with the reagent deposits, such as o-tolidine, on the pyroelectric film sensor strip to produce a yellow color. There are some chemicals, which are reacted in as many as three or four phases of such reaction filters to produce the final product which is measured by a calorimetric reaction with the reagent deposits.

Like the pump, the filters can be engageable with the container 110 containing the selected set of reagent deposits. The filters could optionally be stamped with a bar code such that they may be recognized by the reader 162 with a barcode reading device. This would allow the reader 162 to compensate, or report to the user the use of the filter or the lack of presence of the filter. Furthermore, the filters could optionally be constructed in such a manner that the filter itself would contain or be made of a calorimetric substance that would cause a color change of the filter material showing that the material is being consumed or that it has been fully consumed.

As previously mentioned, the cartridge is mateable with and then detachable from the reading apparatus. When keyably engaged with the reading apparatus, the air channel, cartridge channel, and outlet are fluidly aligned so as to allow for the passage of pumped air therethrough. Alternatively, the reading apparatus may be equipped with a key or piercing mechanism for piercing film sealably applied to the ends of the cartridge channel. Thus, upon proper receipt of the cartridge in the cartridge bay, the reagent deposits may be exposed with an air sample from the local environment. Accordingly, detection and indication of the target gas can occur immediately.

One method employed to "open" or "pierce" the cartridge provides for the unit to contain two hollow pins which are sufficiently long to puncture the bottom of the cartridge at each end providing an air path though the puncture pins themselves. Due to the possible manufacturing difficulty of puncturing the cartridge, one preferred method of cartridge construction would entail a cartridge as shown in FIGS. 3-5. This would be the composite of two plastic plates that, when joined together form a "credit card" shaped plastic device with a hollow interior forming a tunnel or channel through the middle of the device. Prior to assembly of the opposing halves of the cartridge, the embedded pieces would be placed inside the device, then both pieces would be assembled and sealed possibly with a heat seal or a glue.

Figure 6:
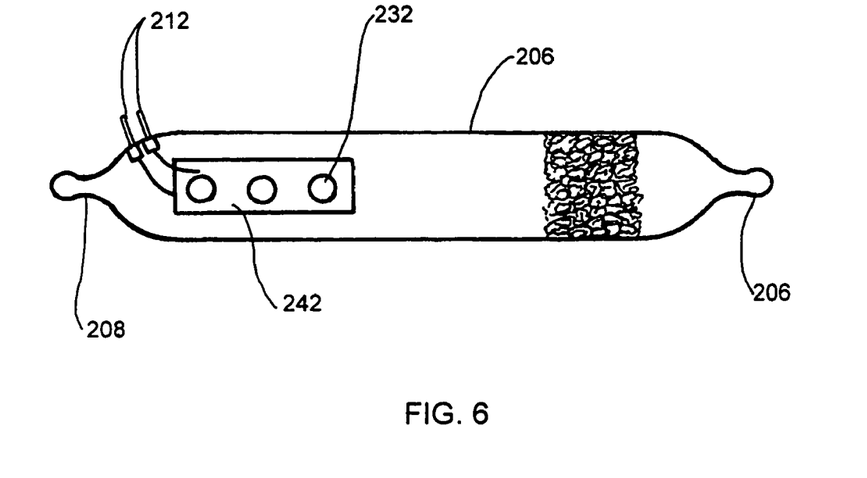
FIG. 6 is a simplified diagram of a detector tube according to the invention.

FIG. 6 depicts yet another embodiment of the invention. In this embodiment, a detector tube 206 is employed to support the carrier 40 during storage and testing. The detector tube 206 is a hermetically-sealed glass tube, structurally similar to those commercially available in the industry. The detector tube has a breakable inlet end 206 and a breakable outlet end 208. The carrier of FIG. 6 includes three reagents spots 232 supported on a polyelectric film transducer 242 and filter material positional upstream thereof. The carrier further includes two wire lead lines 212 that are directed through the walls of the glass tube, thereby providing two electrical connections for a reader.

Figure 7A:
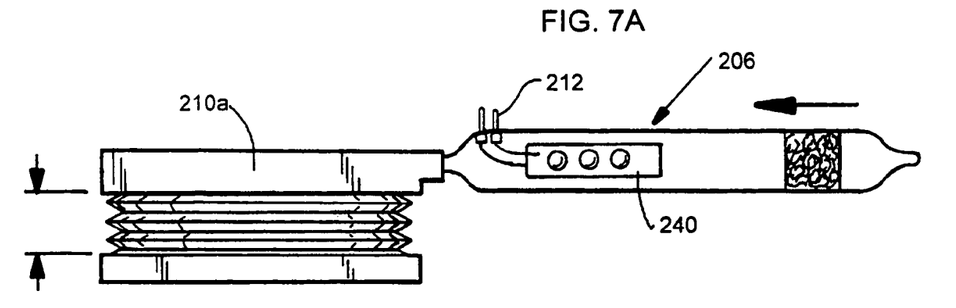
FIG. 7A is a simplified diagram of the detector tube of FIG. 6 engaged with a pump, according to the invention.
Figure 7B:
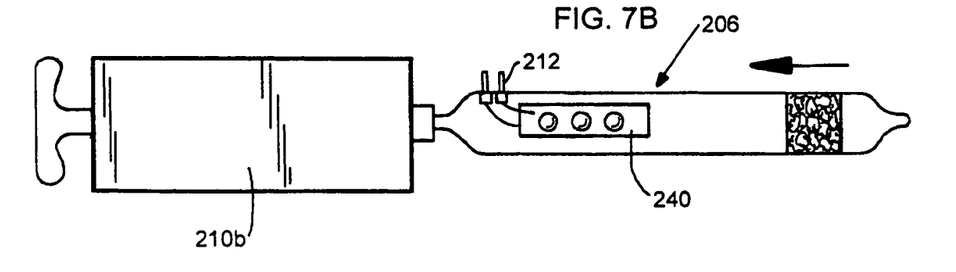
FIG. 7B is a simplified diagram of the detector pump of FIG. 6 engaged with a second type of pump, according to the invention.

FIGS. 7A and 7B depict the detector tube 206 operated with a bellows pump 210a and a manual pump 210b. Either pump may be used in combination with the detector tube 206 to conduct a field testing operation. In particular, the detector tube ends are broken and inserted or engaged with the pump, thereby drawing a sampling of the local environment through the detector tube and past the reagent. Thus, if the reagent is exposed to the target substance, a colorimetric change occurs. The detector tube is then disengaged from the pump and engaged with the appropriate reader such that the connections 212 mate with corresponding connections in the reader. Upon engagement with the reader, one or more LEDS on the reader may be operated to illuminate the reagent (through the glass wall).

Figure 8A:
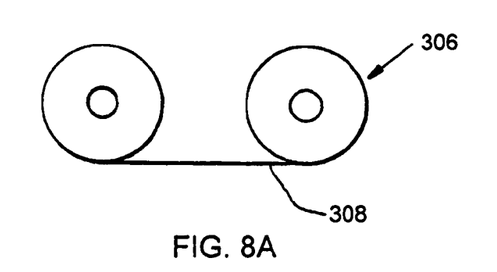
FIG. 8A is a simplified diagram of a third carrier suitable for use with the system.
Figure 8B:
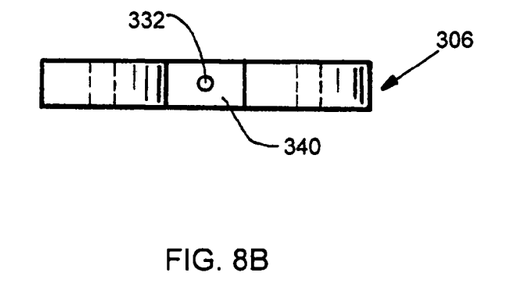
FIG. 8B is simplified plan view of the carrier in FIG. 8A.

FIGS. 8A and 8B depict yet another variation of a carrier for use with the system according to the invention. In particular, FIG. 8 depicts the use of a reel-to-reel tape mechanism 306 for sealingly storing and dispensing individual carriers 340. As shown in FIG. 8B, the reel tape may be segregated into distinct sections, including a section comprising a carrier 340. The carrier will include polyelectric film transducer 342 and one or more reagent deposits 332 thereon. Conveniently, the tape acts to seal the reagent 332 before the reagent 332 is exposed during unwinding, thereby eliminating the need for a sealed container or tunnel. Accordingly, one benefit of the embodiment of FIGS. 8A, 8B is that it allows for "long term" measurement, while preserving the life of the unused reagents.

The roll of tape may include various combinations of reagents or only one type of reagent. Further, the reel-to-reel mechanism may be mounted or housed integrally with a reading device. In the alternative, the reel-to-reel mechanism may be integrated with a fixed testing mechanism rather than a field carryable portable gas detector.

FIG. 9 depicts yet another variation of a carrier for use with the system according to the invention. The carrier of FIG. 9 is a disk type carrier 440 preferably holding a plurality of reagent deposits 432. The reagent deposits 432, as before, will be deposited on and supported by a mat of polyelectric film 442. The polyelectric film 442 may be individual mats or a continuous, circular sheet of film, as shown in FIG. 9.

FIG. 9 also illustrates a reagent deposit sealingly situated in a tunnel 434. The tunnel 434 includes fluid communication inlets (not shown) and outlets 436, which are penetrated and unsealed upon engagement of the disk carrier 440 with the appropriate reader. For example, in FIG. 9, only one reagent deposit remains unsealed, but is positionally engaged with the reader so as to be in alignment with the pumping means provided by the reader. When aligned and in operation, the pump may be operated to draw air from the periphery of the tunnel and past the reagent, towards the center of the disk carrier 440. Upon conclusion of a testing operation, the disk carrier 440 may be rotated so as to align yet another reagent deposit for a subsequent operation. As before, the tunnel 434 may be covered by glass or film, with the ends preferably covered by a puncturable film sheet.

Although the present system, apparatus and method of detecting a target gas and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. For example, various exemplary configurations of a detection apparatus and a reading apparatus have been described. As one of ordinary skill in the art will readily appreciate from the disclosure of the present invention, various elements from measurement or instrumentation technology, or measuring methods or steps, presently existing or later to be developed that perform substantially the same function or achieve substantially the same result as the corresponding embodiments described herein may be utilized according to the present invention. Accordingly, the appended claims are intended to include within their scope such machines, apparatus, methods, or steps.

What is claimed is:

1. A system for measuring the concentration of at least one target substance, said system comprising:
   one or more carriers, at least one of said carriers having
      a plurality of reagent deposits thereon, said reagent deposits being arranged in a plurality of predetermined sets,
      containers wherein each of said sets of reagent deposits is contained, and
      pyroelectric film positioned adjacent said reagent deposits, said pyroelectric film being adapted for detecting heat absorbed in said reagent deposit and correspondingly delivering an output signal; and
   a reader engageable with said carriers and operable to initiate a measurement of the concentration of at least one target substance by exposing a selected set of reagent deposits, said reader being adapted to receive the output signal from said pyroelectric film to convert the output signal into a concentration of the target substance, wherein said carrier is detachable and re-engageable with said reader to initiate exposure of a second set of reagent deposits in a second container.

2. The system of claim 1, wherein said carrier includes a set of reagent deposits having a first reagent deposit for measuring the concentration of a first target substance and a second reagent deposit for measuring the concentration of a second target substance.

3. The system of claim 1, wherein said carrier includes a first set of reagent deposits including a first reagent deposit for measuring the concentration of a first target substance and a second set of reagent deposits including a second reagent deposit for measuring the concentration of a second target substance.

4. The system of claim 1, further comprising means for selecting one of said sets of reagent deposits for exposure to the environment.

5. The system of claim 4, wherein said container includes a cover for sealing the reagent deposits from the environment, and wherein said selecting means includes means engageable with said cover, upon engagement between said carrier and said reader, so as to expose a selected set of reagent deposits.

6. The system of claim 5, wherein said selecting means includes a memory chip included in said carrier.

7. The system of claim 4, said system further comprising:
   a plurality of filters selectively engageable with one or more of said containers for filtering interferences from the environment containing the target substance.

8. The system of claim 1, said system further comprising:
   a plurality of filters selectively engageable with one or more of said containers for filtering interferences from the environment containing the target substance.

9. The system of claim 1, wherein said reagent deposits are deposited directly on said pyroelectric film.

10. The system of claim 5, wherein said container includes two ends and said cover being positioned to cover said two ends.

11. The system of claim 1, further comprising:
    a pump selectively engageable with one or more of said containers such that the environment containing the target substance can be passed through a selected container.

12. The system of claim 11, wherein said pump is continuously operable, said reader includes an optical device intermittently operable to illuminate at least one of said reagent deposits.

13. The system of claim 1, further comprising a rollable tape holding said one or more carriers, said tape being sequentially advanceable so as to expose a reagent deposit.

14. The system of claim 12, wherein said rollable tape is provided on a reel-to-reel mechanism, and wherein one of said reels is provided to support a roll of unused carriers, such that said unused carriers are sealed when supported thereon.

15. A system for measuring the concentration of at least one target substance, said system comprising:
    one or more carriers, said carrier having
       at least one container wherein at least one reagent deposit is deposited, and
       pyroelectric film positioned adjacent said reagent deposit, the pyroelectric film being adapted for detecting heat absorbed by said reagent deposit and correspondingly delivering an output signal;
    a reader engageable with said carrier, said reader being operable to initiate two or more measurements of at least one target substance by exposing said reagent deposit two or more times, said reader being adapted to receive a first output signal from said pyroelectric film corresponding to heat detected by said pyroelectric film and to convert the outputs into a corresponding measurement of the concentration of the target substance; and
    a pump engageable with said containers such that an amount of the environment containing the target substance can be passed through a selected container to expose the reagent deposit to the environment.

16. The system of claim 15, wherein the pump operates at a known flowrate.

17. The system of claim 16, further comprising:
    a measurement device measuring the amount of environment passed through said container, said measuring device being operatively associated with said reader, such that the measured amount can be accounted for in the conversion performed by the reader;
    a timer for timing the length of the use of the pump; and a means for converting the length of the use of the pump into a volume of environment delivered by the pump.

18. The system of claim 17, wherein said containers containing sets of reagent deposits can be used to measure more than one environment by being exposed successively to distinct environments.

19. The system of claim 15, wherein said reader is adapted to convert said output into a corresponding measurement of the target substance by using a known reference of output from the pyroelectric film and comparing the known reference output with output from the pyroelectric film after the reagent deposit has been exposed to the environment containing the target substance.

20. The system of claim 19, wherein said reader is adapted to reset the known reference of output after one or more exposures of the selected sets to a target substance to the last output received from the pyroelectric film prior to converting the output from the pyroelectric film into a measurement of the target substance.

21. The system of claim 17 further comprising
means for selecting one of said sets of reagent deposits for exposure to the environment containing the target substance by selecting one of said containers upon engagement of said carriers with said reader, wherein said carrier is detachable and re-engageable with said reader to initiate exposure of a second set of reagent deposits in a second container.

22. A method of measuring at least one target substance, said method comprising the steps of:
providing a carrier having
at least one container containing a plurality of predetermined sets of reagent deposits, and
pyroelectric film positioned adjacent the reagent deposits, the pyroelectric film being adapted for detecting heat absorbed in a reagent deposit and correspondingly delivering an output signal;
providing a reader engageable with the carrier to initiate a measurement of at least one target substance; and
engaging the carrier with the reader, including
exposing a set of reagent deposits in a selected container by pumping an amount of the environment containing the target substance through the selected container to expose the selected set of reagent deposits to the environment;
receiving an output from the pyroelectric film; and
converting said output into a corresponding measurement of the target substance by using a known reference of output from the pyroelectric film and comparing the known reference output with output from the pyroelectric film after the reagent deposit has been exposed to the environment containing the target substance.

23. The method of claim 22, further comprising the steps of:
measuring the amount of environment pumped, and
accounting for the measured amount in the converting step.

24. The method of claim 23, wherein said measuring step comprises:
accounting the duration of pump operation; and
converting the duration into a volume of environment delivered by the pump.

25. The method of claim 22, further comprising the step of repeating the selecting, exposing, receiving, converting, and pumping steps to measure another environment using a single reagent deposit.

26. The method of claim 22, wherein said converting step includes:
using a known reference of output from the pyroelectric film; and
comparing the known reference output with output from the pyroelectric film after the exposing step.

27. The method of claim 22, further comprising the step of resetting the known reference of output from the pyroelectric film after the exposing step to the last output received from the pyroelectric film.

28. A method of measuring the concentration of at least one target substance present in a gaseous environment, said method comprising the steps of:
providing one or more carriers, at least one of the carriers having at least one reagent deposit; and
pyroelectric film positioned adjacent the reagent deposit, the pyroelectric film being adapted for detecting heat absorbed in a reagent deposit and correspondingly delivering an output signal;
providing a reader engageable with the carrier and operable to initiate a measurement of at least one target substance by exposing the reagent deposit; and
engaging the carrier with the reader, thereby exposing the reagent deposit; and
operating the reader to receive the output signal from the pyroelectric film and converting the output signal into a corresponding measurement of the concentration of the target substance in the environment.

29. The method of claim 28, further comprising the steps of:
disengaging the carrier from the reader; and
repeating each of said selecting, engaging, and operating steps.

30. A system for measuring the concentration of at least one target substance, said system comprising:
a detector tube including a carrier, said carrier having
at least one container wherein at least one reagent deposit is deposited, and
pyroelectric film positioned adjacent said reagent deposit, the pyroelectric film being adapted for detecting heat absorbed by said reagent deposit and correspondingly delivering an output signal;
a reader engageable with said detector tube and said carrier, said reader being operable to initiate measurement of at least one target substance by exposing said reagent deposit, said reader being adapted to receive a first output signal from said pyroelectric film corresponding to heat detected by said pyroelectric film and to convert the outputs into a corresponding measurement of the concentration of the target substance; and
a pump engageable with said containers such that an amount of the environment containing the target substance can be passed through said selected container to expose the reagent deposit to the environment.

31. A system for measuring the concentration of at least one target substance, a carrier engageable with a reader and operable therewith to initiate a measurement of the concentration of the target substance, said carrier comprising:
at least one reagent deposit, said reagent deposit being colorimetrically reactive with the target substance; and
a substrate supporting said reagent deposit, said substrate including
a channel in which said reagent deposit is supported and through which, a sampling of a local environment having the target substance may be passed to expose said reagent deposit, and
a pyroelectric transducer positioned adjacent said reagent deposit, said pyroelectric transducer having a pair of electrodes from which a signal is generated indicative of heat absorbed in said reagent deposit.

32. The system of claim 31, wherein said carrier comprises a channel and includes a cover that sealably contains said reagent deposit therein.

33. The system of claim 32, wherein said pyroelectric transducer is pyroelectric film disposed in said channel adjacent said reagent deposit.

34. The system of claim 32, wherein said channel contains a plurality of reagent deposits.

35. The system of claim 32, wherein said substrate supports a plurality of said channels, each said channel including a cover that sealably contains one or more reagent deposits therein.

36. The system of claim 35, wherein said substrate supports a plurality of predetermined sets of reagent deposits, and each said channel contains one of said predetermined sets.

37. The system of claim 35, wherein said substrate is a circular substrate having a central aperture, each said channel having a first fluid port extending in fluid communication with said central aperture and a second fluid port extending to the periphery of said circular substrate and in fluid communication with the external local environment thereabout.

38. The system of claim 32, wherein said channel has a breakable inlet and a breakable outlet.

39. The system of claim 38, wherein said breakable outlet is connectible with a pump operable to draw a sampling of the local environment through said inlet of said channel.

40. The system of claim 31, wherein said pyroelectric transducer includes pyroelectric film disposed in said channel and a pair of electrodes supported within said substrate.

41. A system for measuring the concentration of at least one target substance in a local environment, said system comprising:

one or more carriers, said carrier including at least one reagent deposit, said reagent deposit being colorimetrically reactive with the target substance, a substrate supporting said reagent deposit, said substrate having a channel in which said reagent deposit is supported and through which a sampling of a local environment having the target substance may be passed to expose said reagent deposit, and a pyroelectric transducer supported by said substrate and in operative association with said reagent deposit to detect heat absorbed by said reagent deposit and correspondingly generate an output signal indicative of the heat detected; and a reader engageable with said carrier to expose said reagent deposit and initiate a measurement of the concentration of the target substance, said reader being operably associated with the carrier to receive said output signal from said carrier and convert said output signal into a corresponding measurement of the concentration of the target substance.

42. The system of claim 1, wherein said carrier includes a plurality of reagent deposits and a plurality of said channels, each said channel including one or more reagent deposits.

43. The system of claim 42, wherein said carrier is detachable and reengagable with said reader to initiate exposure of reagent deposits.

44. The system of claim 41, wherein said channel includes a container sealably containing said reagent deposit therein.

45. The system of claim 44, wherein said system includes a plurality of said channels, each said channel including a plurality of predetermined sets of reagent deposit.

46. The system of claim 45, wherein said carrier includes a first set of reagent deposits including a first reagent deposit for measuring the concentration of a first target substance and a second set of reagent deposits including a second reagent deposit for measuring the concentration of a second target substance.

47. The system of claim 46, further comprising means for selecting one of said sets of reagent deposits for exposure to the environment upon engagement between said carrier and said reader.

48. The system of claim 46, further comprising a plurality of filters selectively engagable with one or more of said containers for filtering interferences from the environment containing the target substance.

49. The system of claim 46, wherein each said reagents deposit is positioned directly on said pyroelectric transducer, and wherein said pyroelectric transducer is a pyroelectric film having a pair of electrodes extending therefrom.

50. The system of claim 46, wherein said carrier includes a pump selectively engagable with one or more said channels such that the environment containing target substance can be passed through a selected channel.

* * * * *